(12) United States Patent
Kraft

(10) Patent No.: US 7,632,790 B2
(45) Date of Patent: Dec. 15, 2009

(54) TRISUBSTITUTED FURANS SUITABLE FOR THE PREPARATION OF FRAGRANCE COMPOSITIONS

(75) Inventor: Philip Kraft, Dubendorf (CH)

(73) Assignee: Givaudan S.A., Vernier (CH)

( * ) Notice: Subject to any disclaimer, the term of this patent is extended or adjusted under 35 U.S.C. 154(b) by 201 days.

(21) Appl. No.: 10/589,654

(22) PCT Filed: Mar. 7, 2005

(86) PCT No.: PCT/CH2005/000137
§ 371 (c)(1),
(2), (4) Date: Apr. 13, 2007

(87) PCT Pub. No.: WO2005/087756
PCT Pub. Date: Sep. 22, 2005

(65) Prior Publication Data
US 2008/0039360 A1    Feb. 14, 2008

(30) Foreign Application Priority Data
Mar. 15, 2004    (GB) ................................ 0405723.8

(51) Int. Cl.
C11D 3/50    (2006.01)

(52) U.S. Cl. ........................ 510/102; 549/429; 549/507; 512/11

(58) Field of Classification Search ................ 549/429, 549/507; 510/102; 512/11
See application file for complete search history.

(56) References Cited

U.S. PATENT DOCUMENTS

| 4,336,197 A | 6/1982 | Fankhauser et al. |
| 4,549,029 A | 10/1985 | Hochstetler |
| 5,034,545 A | 7/1991 | Fischer |

FOREIGN PATENT DOCUMENTS

| WO | WO 96/18710 A | 6/1996 |

OTHER PUBLICATIONS

J. Hartung et al., Journal of the American Chemical Society (2004), vol. 126, issue 38, pp. 12121-12129, Sep. 2004.*
Tang et al., Oxidative Cydization of 5-Hydroxyalkenes With Rhenium Oxide, Utilizing a Co-Oxidant. IV Tetrahedron Letters, 1992, pp. 5303-5306, vol. 33(37), Pergamon Press, Ltd. (GB).
Tang et al. CAS Abstract Acc. No. 1992:651155 for Tetrahedron Letters, 1992, vol. 33(37).
Chastrette et al., Synthese d'oxolannes substitues a partir des tosylates de γ-hydroxycetones, Comptes Rendus des Seances de l'Academie des Sciences, Serie C: Sciences Chimeques, 1980, pp. 305-307. vol. 290(15).
Chastrette et al., CAS Abstract Acc. No. 1980:514218 for Comptes Rendus des Seances de l'Academie des Sciences, Serie C: Sciences Chimeques, 1980, vol. 290(15).
Goldfinger, Reactions od Halogen Atoms, Pure and Applied Chemistry, 1962, pp. 423-440, vol. 5, Pergamon Press, Oxford GB.
Walling et al., Positive Halogen Compounds. VII. Intramolecular Chlorinations with Long Chain Hypochlorites, Journal of the American Chemical Society, 1963, pp. 1597-1601, vol. 85.
Walling et al., CAS Abstract Acc. No. 1963:408397 for Journal of the American Chemical Society, 1963, vol. 85.
WPI Abstract Acc. No. 1996-300631 [30] for WO96/18710A (Lion Corporation), Jun. 20, 1996.

* cited by examiner

*Primary Examiner*—John R Hardee
(74) *Attorney, Agent, or Firm*—Curatolo Sidoti Co., LPA; Joseph G. Curatolo; Peter R. Detorre

(57) ABSTRACT

2,2-Disubstituted 5-methyl-2,5-dihydro- and 2,2-disubstituted 5-methyl-tetrahydrofurans of formula (I)

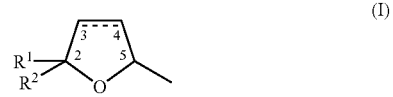

(I)

wherein $R^1$ is methyl, ethyl, propyl or iso-propyl; and $R^2$ is a branched $C_4$-$C_7$ alkyl, $C_5$-$C_8$ cycloalkyl, or mono- or disubstituted $C_5$ or $C_6$ cycloalkyl; and
the bond between C-3 and C-4 is a single bond, or the dotted line together with the bond between C-3 and C-4 represents a double bond are useful as odorants.

15 Claims, No Drawings

TRISUBSTITUTED FURANS SUITABLE FOR THE PREPARATION OF FRAGRANCE COMPOSITIONS

CROSS REFERENCE TO RELATED APPLICATIONS

This application is a national stage application of International Application No. PCT/CH2005/000137, filed 7 Mar. 2005, which claims the benefit of Application No. GB0405723.8, filed 15 Mar. 2004, from which applications priority is claimed.

The present invention relates to trisubstituted furans, namely 2,2-disubstituted 5-methyl-2,5-dihydro- and 2,2-disubstituted 5-methyl-tetrahydrofurans and their use as odorants. This invention relates furthermore to a method of their production and to fragrance compositions comprising them.

In the fragrance industry there is a constant demand for new compounds that enhance or improve on odour notes, or impart new odour notes.

It has now been found that certain trisubstituted furans constitute new powerful blackcurrant odorants devoid of any sulphur off-notes. Fruity, blackcurrant notes were first used in >>Amazone<< (Hermes, 1974), and became more and more trendy as top notes in perfumery as they can impart naturalness and freshness, and thus constitute attractive alternatives to hesperidic-citrus, lavender or aldehydic notes. Perfume examples for this recent trend include >>Le Monde est beau<< (Kenzo, 1997) and >>In Love Again<< (Yves Saint Laurent, 1998). Since then, blackcurrant notes became very popular and are today widely used, not only in fine fragrances, but also in the cosmetics and toiletries segment. However, most blackcurrant odorants, such as Corps Cassis (4-methyl-4-methylsulfanylpentan-2-one) and Oxane (2-methyl-4-propyl[1,3]oxathiane) are sulphury compounds and intense, sulfury-smelling by-products which may lead to unpleasant off-notes. Thus, there is a specific need for new blackcurrant odorants devoid of sulphur.

Accordingly, the present invention refers in one of its aspects to a compound of formula (I)

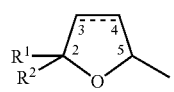

(I)

wherein
$R^1$ is methyl, ethyl, propyl or iso-propyl;
$R^2$ is a branched $C_4$-$C_7$ alkyl, e.g. tert-butyl, neopentyl, or iso-hexyl; $C_5$-$C_8$ cycloalkyl, e.g. cyclohexane and cycloheptane; or mono- or disubstituted $C_5$ or $C_6$ cycloalkyl, such as methylcyclohexyl and dimethylcyclohexyl; and
the bond between C-3 and C-4 is a single bond, or the dotted line together with the bond between C-3 and C-4 represents a double bond.

The compounds according to the present invention contain several chiral centres, and as such may exist as a mixture of stereoisomers, or they may be resolved as isomerically pure forms. Resolving stereoisomers adds to the complexity of manufacture and purification of these compounds, and so it is preferred to use the compounds as mixtures of their stereoisomers simply for economic reasons. However, if it is desired to prepare individual stereoisomers, this may be achieved according to methodology known in the art, e.g. preparative HPLC and GC or by stereoselective synthesis.

Particular preferred compounds of formula (I) are 2-tert-butyl-5-methyl-2-propyl-2,5-dihydrofuran, 2-tert-butyl-5-methyl-2-propyltetrahydrofuran, 2-tert-butyl-2-isopropyl-5-methyl-2,5-dihydrofuran, 2-tert-butyl-2-isopropyl-5-methyltetrahydrofuran, 2-tert-butyl-2-ethyl-5-methyl-2,5-dihydrofuran, 2-tert-butyl-2-ethyl-5-methyltetrahydrofuran, 2-tert-butyl-2,5-dimethyl-2,5-dihydrofuran, 2-tert-butyl-2,5-dimethyltetrahydrofuran, 2-(3',3'-dimethylcyclohexyl)-2,5-dimethyl-2,5-dihydrofuran, and 2-(3',3'-dimethylcyclohexyl)-2,5-dimethyltetrahydrofuran.

The compounds according to the present invention may be used alone or in combination with a base material. As used herein, the "base material" includes all known odorant molecules selected from the extensive range of natural products and synthetic molecules currently available, such as essential oils, alcohols, aldehydes and ketones, ethers and acetals, esters and lactones, hetero- and macrocycles, as well as nitrogen-containing compounds, and/or in admixture with one or more ingredients or excipients conventionally used in conjunction with odorants in fragrance compositions, for example, carrier materials, and other auxiliary agents commonly used in the art.

The following list comprises examples of known odoriferous molecules, which may be combined with the compounds of the present invention:

essential oils and extracts, e.g. angelica root oil, bergamot oil, blackcurrant absolute, buchu leaf oil, coriander oil, geranium oil, grapefruit oil, jasmine absolute, lavender oil, lime oil, neroli oil, oakmoss absolute, orris root oil, patchouli oil, petitgrain oil, rose oil, or ylang-ylang oil.

alcohols, e.g. citronellol, dimethyl benzyl carbinol, eugenol, geraniol, (3Z)-hex-3-enol, linalool, phenylethyl alcohol, Super Muguet®, terpineol, or Undecavertol®.

aldehydes and ketones, e.g. Cetone V™, damascenone, heliotropine, α-hexylcinnam aldehyde, Iso E Super®, β-ionone, Isoraldeine®, Silvial®, or vanillin.

ethers and acetals, e.g. Ambrox™, Oxane™ or Spirambrene™.

esters and lactones, e.g. benzyl acetate, coumarin, Hedione®, or hexyl salicylate.

hetero- and macrocycles, e.g. ambrettolide, ethylene brassylate, Exaltolide®, maltol, Moxalone™, or Nirvanolide®.

nitrogen-containing compounds, e.g. methyl anthranilate, Peonile®, or Stemone®.

The compounds of the present invention may be used in a broad range of fragrance applications, e.g. in any field of fine and functional perfumery, such as perfumes, household products, laundry products, body care products and cosmetics. The compounds can be employed in widely varying amounts, depending upon the specific application and on the nature and quantity of other odorant ingredients. The proportion is typically from 0.001 to 5 weight percent of the application. In one embodiment, compounds of the present invention may be employed in a fabric softener in an amount of from 0.001 to 0.05 weight percent. In another embodiment, compounds of the present invention may be used in fine perfumery in amounts of from 0.1 to 5 weight percent, more preferably between 0.1 and 2 weight percent. However, these values are given only by way of example, since the experienced perfumer may also achieve effects or may create novel accords with lower or higher concentrations.

The compounds of the present invention may be employed into the fragrance application simply by directly mixing the fragrance composition with the fragrance application, or they may, in an earlier step, be entrapped with an entrapment material, examples of which include polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the application.

Thus, the invention additionally provides a method of manufacturing a fragrance application, comprising the incorporation of a compound of formula (I) as a fragrance ingredient, either by directly admixing the compound to the application or by admixing a fragrance composition comprising a compound of formula (I), which may then be mixed to a fragrance application, using conventional techniques and methods.

As used herein, "fragrance application" means any products, such as fine fragrances, e.g. eau de perfumes and eau de toilettes; household products, e.g. detergents for dishwasher, surface cleaner; laundry products, e.g. softener, bleach, detergent; body care products, e.g. shampoo, shower gel; and cosmetics, e.g. deodorants, vanishing cremes, comprising an odorant. This list of products is given by way of illustration and is not to be regarded as being in any way limiting.

Compounds of formula (I) may be prepared by the reaction of magnesium Grignard reagent of 3-butyn-2-ol, prepared according to a general procedure well known in the art, with a corresponding ketone ($R^1R^2CO$) resulting in an alkynediol. The alkynediol is then hydrogenated in the presence of a Lindlar catalyst. Subsequent cyclisation of the formed cis-configurated alkenediol in the presence of potassium hydrogensulfate results in the formation of the corresponding 5-methyl-2,5-dihydrofurane. Further compounds of formula (I) may be prepared by hydrogenation of the dihydrorfuranes.

The invention is now further described with reference to the following non-limiting examples.

EXAMPLE 1

2-tert-Butyl-5-methyl-2-propyl-2,5-dihydrofuran

Over a period of 30 min, a solution of 40.7 g (374 mmol) of ethyl bromide in 100 mL of dry tetrahydrofuran was added dropwise to a stirred suspension of 9.08 g (374 mmol) of magnesium turnings in 5 mL of dry tetrahydrofuran, with the reaction being initiated by occasional heating with a heat gun. The reaction mixture was then stirred for additional 3 h at reflux. The reaction was allowed to cool down to room temp., and a solution of 12.6 g (180 mmol) of but-3-yn-2-ol in 80 mL of dry tetrahydrofuran was added dropwise with stirring. The reaction mixture was then again heated to reflux for 4 h, prior to removal of the heating bath. At room temp., a solution of 25.0 g (195 mmol) of 2,2-dimethylhexan-3-one in 90 mL of dry tetrahydrofuran was added with stirring within 35 min, and the reaction mixture was refluxed for another 2 d with stirring. The reaction mixture was then allowed to cool to room temp., and quenched with 500 mL of an aqueous satd. $NH_4Cl$ solution. The aqueous layer was extracted three times with 500 mL of ether each, the combined organic extracts were dried with sodium sulfate, and the solvent was evaporated on a rotary evaporator to provide 32.3 g (90%) of crude 5-tert-butyloct-3-yne-2,5-diol as a slightly yellowish oil, which was employed without further purification. A solution of 20.8 g (105 mmol) of this product in 300 mL of ethanol was hydrogenated by stirring at ambient pressure and temp. in an atmosphere of hydrogen in the presence of 3.11 g (2.92 mmol) of 10% palladium on barium sulfate and 300 mg (2.32 mmol) of quinoline. After 10 h of stirring, the catalyst was filtered off over a pad of Celite, and the solvent was removed on a rotary evaporator to provide 20.7 g (99%) of crude (3Z)-5-tert-butyloct-3-ene-2,5-diol, of which 19.6 g (98 mmol) was heated for 45 min in a Kugelrohr apparatus to 155° C./280 mbar in the presence of 2.00 g (14.7 mmol) of $KHSO_4$. The evaporating reaction product was trapped in a bulb at –80° C., and further purified by flash chromatography (400 g of silica-gel, pentane/ether, 98:2) to afford 7.26 g of product. This was then distilled in a Kugelrohr apparatus to furnish at 70-80° C./20 mbar 6.24 g (34%) of the title compound as a colorless odoriferous liquid.

IR (film): ν=1110/1047 (ν C—O—C), 1365/1353 ($δ_s$ $CH_3$), 977 (δ C=C—H), 1466/1480 ($δ_{as}$ $CH_3$), 1715 (ν C=C, ring), 3074 (ν C=C—H) $cm^{-1}$.-$^1$H NMR ($CDCl_3$): δ=0.88/0.91 (t, J=7.0 Hz, 3H, 3"-$H_3$), 0.90 (s, 9H, 1'-$Me_3$), 1.23/1.25 (2d, J=6.5 Hz, 3H, 5-Me), 1.42-1.50 (m, 2H, 2"-$H_2$), 1.68-1.74 (m, 2H, 1"-$H_2$), 4.87-4.88 (m, 1H, 5-H), 5.55/5.57 (2dd, J=6.0, 2.5 Hz, 1H, 4-H), 5.70/5.72 (2d, J=6.0 Hz, 1H, 3-H).-$^{13}$C NMR ($CDCl_3$): δ=14.9/15.0 (2q, C-3"), 17.2/17.4 (2t, C-2"), 18.4/18.7 (2q, 5-Me), 21.4/21.8 (2t, C-1"), 26.1/26.7 (2q, 1'-$Me_3$), 35.5/37.2 (2s, C-1'), 82.8/82.9 (2d, C-5), 98.4/98.6 (2s, C-2), 130.2/130.5/131.2/131.7 (4d, C-3, -4).-MS (EI): m/e (%)=57 (17) [$C_4H_9^+$], 83 (9) [$C_5H_7O^+$], 125 (100) [$M^+$-$C_4H_9$], 139 (8) [$M^+$-$C_3H_7$], 167 (5) [$M^+$-$CH_3$].

Odor description: Blackcurrant, natural, rich, eucalyptus buds, anis, buchu leaves, slightly green.

EXAMPLE 2

2-tert-Butyl-5-methyl-2-propyltetrahydrofuran

At ambient temp., a suspension of 2.91 g (10.4 mmol) of 2-tert-butyl-5-methyl-2-propyl-2,5-dihydrofuran and 1.06 g (1.00 mmol) of 10% palladium on activated charcoal in 60 mL of dry ether was hydrogenated for 4 h in a Parr apparatus at 2.5 bar hydrogen pressure. The catalyst was filtered off over a pad of Celite, and the solvent evaporated. The resulting residue was distilled in a Kugelrohr apparatus to provide at 75-85° C./20 mbar 2.43 g (80%) of the title compound as a colorless odoriferous liquid.

IR (film): ν=1110/1088 (ν C—O—), 1379/1365 (65 $CH_3$), 1466/1480 (5 as $CH_3$), 985 ($ν_r$ $CH_2$) $cm^{-1}$.-$^1$H NMR ($CDCl_3$): δ=0.88/0.91 (t, J=7.0 Hz, 3H, 3"-$H_3$), 0.90 (s, 9H, 1'-$Me_3$), 1.19/1.21 (2d, J=6.0 Hz, 3H, 5-Me), 1.33-1.40 (m, 2H, 2"-$H_2$), 1.41-1.45 (m, 2H, 1"-$H_2$), 1.69-1.76 (m, 2H, 3-$H_2$), 1.79-1.88 (m, 2H, 4-$H_2$), 4.05 (br. quint., J=6.0 Hz, 1H, 5-H).-$^{13}$C NMR ($CDCl_3$): δ=15.2/15.3 (2q, C-3"), 18.0/18.2 (2t, C-2"), 21.2/21.3 (2q, 5-Me), 26.3/26.3 (2q, 1'-$Me_3$), 31.2/31.5 (2t, C-4), 35.7/36.0 (2t, C-3), 38.2/38.7 (2t, C-1"), 39.5/39.6 (2s, C-1'), 76.6/77.0 (2d, C-5), 89.0/90.2 (2s, C-2).-MS (EI): m/e (%)=57 (30) [$C_4H_9^+$], 71 (100) [$M^+$-$C_8H_{17}$], 85 (6) [$C_4H_9O^+$], 127 (76) [$M^+$-$C_4H_9$], 141 (5) [$M^+$-$C_3H_7$], 169 (5) [$M^+$-$CH_3$].

Odor description: Blackcurrant, damascone, sweet, natural, rich, with green, piny, eucalyptus and mint-like facets.

EXAMPLE 3

2-tert-Butyl-2-isopropyl-5-methyl-2,5-dihydrofuran

Following the general procedure of example 1, 5-isopropyl-6,6-dimethylhept-3-yne-2,5-diol was prepared in 78% yield by reaction of 2,2,4-trimethylpentan-3-one with the previously prepared Grignard reagent of but-3-yn-2-ol. Lindlar hydrogenation of a solution of 18.1 g (90.0 mmol) of this material in 300 mL of dry ethanol in the presence of 2.20 g (2.07 mmol) of 10% palladium on barium sulfate and 320 mg (2.48 mmol) of quinoline according to example 1 provided after analogous work-up 17.9 g (99%) of (3Z)-5-isopropyl-6,6-dimethylhept-3-ene-2,5-diol, of which 17.2 g (85 mmol) was heated in a Kugelrohr apparatus to 155° C./280 mbar in the presence of 1.71 g (12.5 mmol) of $KHSO_4$ to furnish after trapping of the evaporating product at −80° C. and flash chromatography (400 g of silica gel, pentane/ether, 98:2) 8.32 g of a colorless oil. This product was further purified by Kugelrohr distillation to afford at 80-90° C./20 mbar 7.52 g (48%) of the title compound as a colorless odoriferous liquid.

IR (film): ν=1111/1079 (ν C—O—C), 1366/1353 ($δ_s$ $CH_3$), 983 (δ C═C—H), 1468/1481 ($δ_{as}$ $CH_3$), 1712 (ν C═C, ring), 3071 (ν C═C—H) $cm^{-1}$.-$^1$H NMR ($CDCl_3$): δ=0.88/0.89/0.91/0.92 (4d, J=6.0 Hz, 6H, 1"-$Me_2$), 0.95 (s, 9H, 1'-$Me_3$), 1.23/1.26 (2d, J=6.5 Hz, 3H, 5-Me), 2.12/2.26 (m, 1H, 1"-H), 4.80-4.86 (m, 1H, 5-H), 5.67/5.68 (2dd, J=6.0, 2.5 Hz, 1H, 4-H), 5.73/5.75 (2d, J=6.0 Hz, 1H, 3-H).-$^{13}$C NMR ($CDCl_3$): δ=19.6/19.7 (2q, 5-Me), 20.6/20.8/21.3/21.7 (4q, 1"-$Me_2$), 26.5/27.2 (2q, 1'-$Me_3$), 31.4/34.1 (2d, C-1"), 37.6/40.6 (2s, C-1'), 82.1/82.2 (2d, C-5), 99.6/99.7 (2s, C-2), 128.5/128.6/130.4/131.1 (4d, C-3, -4).-MS (EI): m/e (%)=57 (100) [$C_4H_9^+$], 83 (45) [$C_5H_7O^+$], 125 (67) [$M^+$-$C_4H_9$], 139 (56) [$M^+$-$C_3H_7$], 167 (5) [$M^+$-$CH_3$].

Odor description: Blackcurrant, fruity, grape, fresh with slightly metallic green nuances.

EXAMPLE 4

2-tert-Butyl-2-isopropyl-5-methyltetrahydrofuran

Following the general procedure of example 2, 2-tert-butyl-2-isopropyl-5-methyltetrahydrofuran was prepared from 3.61 g (19.8 mmol) of 2-tert-butyl-2-isopropyl-5-methyl-2,5-dihydrofuran by hydrogenation in the presence of 1.21 g (1.14 mmol) of 10% palladium on activated charcoal. Purification of the crude product by Kugelrohr distillation at 85-95° C./20 mbar furnished 3.42 g (93%) of the title compound as a colorless odoriferous liquid.

IR (film): ν=1085 (ν C—O—C), 993 ($ν_r$ $CH_2$), 1382/1366 ($δ_s$ $CH_3$), 1478 ($δ_{as}$ $CH_3$) $cm^{-1}$.-$^1$H NMR ($CDCl_3$): δ=0.89/0.92 (2d, J=6.5 Hz, 6H, 1"-$Me_2$), 0.94 (s, 9H, 1'-$Me_3$), 1.19/1.23 (2d, J=6.0 Hz, 3H, 5-Me), 1.75-1.79 (m, 2H, 4-$H_2$), 1.80-1.88 (m, 2H, 3-$H_2$), 2.06/2.25 (2 sept., J=7.0 Hz, 1H, 1"-H), 3.97-4.05 (m, 1H, 5-H).-$^{13}$C NMR ($CDCl_3$): δ=19.7/20.6 (2q, 5-Me), 20.6/20.7/20.8/20.9 (4q, 1"-$Me_2$), 26.8/27.0 (2q, 1'-$Me_3$), 27.1/27.2 (2t, C-4), 29.2/33.3 (2d, C-1"), 34.4/35.9 (2t, C-3), 39.1/40.1 (2s, C-1'), 75.8/76.0 (2d, C-5), 91.8/92.4 (2s, C-2).-MS (EI): m/e (%)=57 (95) [$C_4H_9^+$], 71 (100) [$M^+$-$C_8H_{11}$], 85 (17) [$C_5H_9O^+$], 127 (61) [$M^+$-$C_4H_9$], 141 (77) [$M^+$-$C_3H_7$], 169 (5) [$M^+$-$CH_3$].

Odor description: Blackcurrant, fruity, green, sweet, coumarin-like with floral and camphoraceous undertones.

EXAMPLE 5

2-tert-Butyl-2-ethyl-5-methyl-2,5-dihydrofuran

Following the general procedure of example 1, 5-ethyl-6,6-dimethylhept-3-yne-2,5-diol was prepared in 83% yield by reaction of 2,2-dimethylpentan-3-one with the previously prepared Grignard reagent of but-3-yn-2-ol. Lindlar hydrogenation of a solution of 32.1 g (161 mmol) of this material in 400 mL of dry ethanol in the presence of 2.81 g (2.64 mmol) of 10% palladium on barium sulfate and 1.05 g (8.12 mmol) of quinoline provided after standard work-up 31.4 g (97%) of (3Z)-5-ethyl-6,6-dimethylhept-3-ene-2,5-diol, of which 21.2 g (112 mmol) was cyclised at 155° C./280 mbar in the presence of 2.55 g (18.7 mmol) of $KHSO_4$ to afford after purification by flash chromatography (600 g of silica gel, pentane/ether, 98:2) 10.1 g of the corresponding dihydrofuran. Distillation at 70-80° C./20 mbar provided 6.62 g (36%) of the title compound as a colorless odoriferous liquid.

IR (film): ν=1102/1084 (ν C—O—C), 967 (δ C═C—H), 1365/1352 (8, $CH_3$), 1465/1479 ($δ_{as}$ $CH_3$), 1705 (ν C═C, ring), 3073 (ν C═C—H) $cm^{-1}$.-$^1$H NMR ($CDCl_3$): δ=0.77/0.81 (2t, J=7.5 Hz, 3H, 2"-$H_3$), 0.91/0.93 (2s, 9H, 1'-$Me_3$), 1.24/1.26 (2d, J=6.5 Hz, 3H, 5-Me), 1.53-1.65 (m, 2H, 1"-$H_2$), 4.82-4.93 (m, 1H, 5-H), 5.54/5.56 (2dd, J=6.0, 2.5 Hz, 1H, 4-H), 5.74/5.76 (2d, J=6.0 Hz, 1H, 3-H).-$^{13}$C NMR ($CDCl_3$): δ=8.1/9.3 (2q, C-2"), 21.1/21.4 (2q, 5-Me), 24.9/26.8 (2t, C-1"), 25.8/27.4 (2q, 1'-$Me_3$), 36.6/39.4 (2s, C-1'), 82.5/82.8 (2d, C-5), 98.4/98.7 (2s, C-2), 129.3/129.8/131.2/131.8 (4d, C-3, -4).-MS (EI): m/e (%)=57 (26) [$C_4H_9^+$], 83 (6) [$C_5H_7O^+$], 111 (100) [$M^+$-$C_4H_9$], 139 (9), [$M^+$-$C_2H_5$], 153 (3) [$M^+$-$CH_3$].

Odor description: Camphoraceous, fruity, blackcurrant, fresh, with green-metallic and animalic nuances.

EXAMPLE 6

2-tert-Butyl-2-ethyl-5-methyltetrahydrofuran

Analogous to the procedure of example 2, by hydrogenation of 3.12 g (18.4 mmol) of 2-tert-butyl-2-isopropyl-5-methyl-2,5-dihydrofuran in the presence of 1.20 g (1.12 mmol) of 10% palladium on activated charcoal. Kugelrohr distillation of the reaction product provided at 70-80° C./20 mbar 3.42 g (93%) of the title compound as a colorless odoriferous liquid.

IR (film): ν=1106/1083 (ν C—O—C), 977 ($ν_r$ $CH_2$), 1364/1380 ($δ_s$ $CH_3$), 1479 ($δ_{as}$ $CH_3$) $cm^{-1}$.-$^1$H NMR ($CDCl_3$): δ=0.84-0.95 (m, 3H, 2"-$H_3$), 0.90/0.92 (2s, 9H, 1'-$Me_3$), 1.20/1.22 (2d, J=8.0 Hz, 3H, 5-Me), 1.36-1.46 (m, 2H, 3-$H_2$), 1.58-1.76 (m, 2H, 1"-$H_2$), 1.79-1.93 (m, 2H, 4-$H_2$), 3.94-4.11 (m, 1H, 5-H).-$^{13}$C NMR ($CDCl_3$): δ=8.9/9.0 (2q, C-2"), 20.9/21.0 (2q, 5-Me), 26.0/26.5 (2q, 1'-$Me_3$), 27.9/28.0 (2t, C-1"), 28.7/30.2 (2t, C-3), 35.3/35.8 (2t, C-4), 38.0/39.3 (2s, C-1'), 76.5/76.7 (2d, C-5), 89.8/90.1 (2s, C-2).-MS (EI): m/e (%)=57 (100) [$C_4H_9^+$], 85 (7) [$C_5H_9O^+$], 113 (59) [$M^+$-$C_4H_9$], 141 (21) [$M^+$-$C_2H_5$], 153 (5) [$M^+$-$CH_3$].

Odor description: Fruity, minty, camphoraceous, blackcurrant, with metallic and animalic undertones.

EXAMPLE 7

2-tert-Butyl-2,5-dimethyl-2,5-dihydrofuran

Following the general procedure of example 1, 5,6,6-trimethylhept-3-yne-2,5-diol was prepared in 96% yield by reaction of 3,3-dimethylbutan-2-one with the previously prepared Grignard reagent of but-3-yn-2-ol. Lindlar hydrogenation of 10.2 g (60.0 mol) of a solution of this material in 200 mL of dry ethanol in the presence of 960 mg (0.90 mmol) of 10% palladium on barium sulfate and 360 mg (2.78 mmol) of quinoline provided after the usual work-up 10.2 g (100%) (3Z)-5,6,6-trimethylhept-3-ene-2,5-diol, of which 9.80 g (57.0 mmol) was cyclized in a Kugelrohr apparatus at 155° C./280 mbar in the presence of 1.14 g (8.37 mmol) of $KHSO_4$ to afford after flash chromatography (200 g of silica gel, pentane/ether, 98:2) 2.61 g of the corresponding dihydrofuran. Distillation in vacuo at 45-50° C./20 mbar provided 2.35 g (26%) of the title compound as colorless odoriferous liquid.

IR (film): ν=1102/1095 (ν C—O—C), 1367/1350 ($δ_s$ $CH_3$), 946 (δ C═C—H), 1454/1479 ($δ_{as}$ $CH_3$), 1709 (ν C═C, ring), 3075 (ν C═C—H) $cm^{-1}$.-$^1$H NMR ($CDCl_3$):

δ=0.91/0.92 (2s, 9H, 1'-Me₃), 1.21/1.22 (2s, 3H, 2-Me), 1.24/ 1.26 (2d, J=6.5 Hz, 3H, 5-Me), 4.82-4.92 (m, 1H, 5-H), 5.56/5.62 (2dd, J=6.0, 1.5 Hz, 1H, 4-H), 5.76/5.79 (2d, J=6.0 Hz, 1H, 3-H).-$^{13}$C NMR (CDCl₃): δ=20.9/21.1 (2q, 5-Me), 23.3/24.2 (2q, 2-Me), 25.7/26.1 (2q, 1'-Me₃), 36.2/38.3 (2s, C-1'), 80.1/82.4 (2d, C-5), 95.0/95.2 (2s, C-2), 129.8/130.4/ 132.1/132.7 (4d, C-3, -4).-MS (EI): m/e (%)=57 (10) [$C_4H_9^+$], 83 (5) [$C_5H_7O^+$], 97 (100) [$M^+$-$C_4H_9$], 139 (5) [$M^+$-$CH_3$].

Odor description: Blackcurrant, citric, limette, green and slightly fatty.

EXAMPLE 8

2-tert-Butyl-2,5-dimethyltetrahydrofuran

According to the procedure of example 2, by hydrogenation of 1.62 g (10.3 mmol) of 2-tert-butyl-2,5-dimethyl-2,5-dihydrofuran in the presence of 600 mg (0.56 mmol) of 10% palladium on activated charcoal. Kugelrohr distillation furnished at 45-50° C./20 mbar 1.37 g (82%) of the title compound as a colorless odoriferous liquid.

IR (film): ν=1102 (ν C—O—C), 1368/1380 ($\delta_s$ CH₃), 1473/1478 ($\delta_{as}$ CH₃), 953 ($\nu_r$ CH₂) cm$^{-1}$.-$^1$H NMR (CDCl₃): δ=0.92 (s, 9H, 1'-Me₃), 1.13/1.15 (2s, 3H, 2-Me), 1.19/1.21 (2d, J=6.0 Hz, 3H, 5-Me), 1.32-1.57 (m, 2H, 3-H₂), 1.98-2.01 (m, 2H, 4-H₂), 3.88-4.12 (m, 1H, 5-H).-$^{13}$C NMR (CDCl₃): δ=20.9/22.4 (2q, 5-Me), 22.1/24.3 (2q, 2-Me), 25.7 (q, 1'-Me₃), 26.5/27.3 (2t, C-3), 33.9/34.4 (2t, C-4), 36.8/37.8 (2s, C-1'), 73.6 (d, C-5), 87.6 (s, C-2).-MS (EI): m/e (%)=57 (28) [$C_4H_9^+$], 85 (5) [$C_4H_9O^+$], 99 (100) [$M^+$-$C_4H_9$], 141 (8) [$M^+$-$CH_3$].

Odor description: Green, camphoraceous, blackcurrant-like with some slight reminiscence to orange blossoms.

EXAMPLE 9

2-(3',3'-Dimethylcyclohexyl)-2,5-dimethyl-2,5-dihydrofuran

Following the general procedure of example 1, 2-(3',3'-dimethylcyclohexyl)hex-3-yne-2,5-diol was prepared in 62% yield by reaction of 1-(3',3'-dimethylcyclohexyl)ethanone with the previously prepared Grignard reagent of but-3-yn-2-ol. Lindlar hydrogenation of 10.0 g (44.6 mmol) of a solution of this material in 250 mL of dry ethanol in the presence of 740 mg (0.695 mmol) of 10% palladium on barium sulfate and 290 mg (2.24 mmol) of quinoline provided after the usual work-up 9.82 g (97%) (3Z)-2-(3',3'-dimethyl-cyclohexyl)hex-3-ene-2,5-diol, which was cyclized in a Kugelrohr apparatus at 180° C./20 mbar in the presence of 430 mg (3.16 mmol) of KHSO₄. The resulting product was purified by flash chromatography (200 g of silica gel, pentane/ether, 99:1) and subsequent Kugelrohr distillation to provide at 55-60° C./0.1 mbar 1.46 g (16%) of the title compound as colorless odoriferous liquid.

IR (film): ν=824 (δ C=C—H), 1085/1105 (ν C—O—C), 1366/1350 ($\delta_s$ CH₃), 970 ($\nu_r$ CH₂), 1453 ($\delta_{as}$ CH₃) cm$^{-1}$.-$^1$H NMR (CDCl₃): δ=0.84-1.74 (m, 9H, 1'-H, 2'-,4'-,5'-,6'-H₂), 0.87/0.88/0.90/0.91 (2s, 6H, 3'-Me₂), 1.20/1.21 (2s, 3H, 2-Me), 1.24/1.25/1.25/1.26 (4d, J=6.5 Hz, 3H, 5-Me), 4.81-4.92 (m, 1H, 5-H), 5.62/5.64/5.64/5.65 (4dd, J=6.0, 1.5 Hz, 1H, 4-H), 5.67/5.68/5.69/5.70 (4d, J=6.0 Hz, 1H, 3-H).-$^{13}$C NMR (CDCl₃): δ=14.0/21.5/21.6/22.3 (4q, 5-Me), 22.3/22.4 (2t, C-5'), 23.2/23.9/24.6/24.7/26.6/28.2 (6q, 2-Me, 3'-Me axial), 27.2/27.8/28.2 (4t, C-6'), 30.7/30.8 (2s, C-3'), 33.6/34.1 (2q, 3'-Me equat.), 39.1/39.2 (2t, C-2'), 40.7/41.4 (2t, C-4'), 42.3/42.5/43.4/43.5 (4d, C-1'), 79.9/80.0/81.7/81.8 (4d, C-5), 92.3/92.4/92.5/92.6 (4s, C-2), 129.9/130.0/130.4/ 130.5/132.1/132.2/132.6/133.0 (8d, C-3, -4).-MS (EI): m/e (%)=43 (14) [$C_3H_7^+$], 55 (6) [$C_4H_7^+$], 69 (6) [$C_5H_9^+$], 79 (4) [$M^+$-$C_8H_{15}$—H₂O], 97 (100) [$M^+$-$C_8H_{15}$], 175 (1) [$M^+$-$CH_3$—$CH_3$], 193 (1) [$M^+$-$CH_3$], 208 (1) [$M^+$].

Odor description: Fruity, blackcurrant, grapefruit, natural, green tomato vine, with aspects of apple and rhubarb.

EXAMPLE 10

2-(3',3'-Dimethylcyclohexyl)-2,5-dimethyltetrahydrofuran

According to the procedure of example 2, by hydrogenation of 1.00 g (4.80 mmol) of 2-(3',3'-dimethylcyclohexyl)-2,5-dimethyl-2,5-dihydrofuran in the presence of 100 mg (0.0940 mmol) of 10% palladium on activated charcoal. Kugelrohr distillation furnished at 65-70° C./0.1 mbar 690 mg (68%) of the title compound as a colorless odoriferous liquid.

IR (film): ν=1094 (ν C—O—C), 953 ($\nu_r$ CH₂), 1455 ($\delta_{as}$ CH₃), 1374 (3, CH₃) cm$^{-1}$.-$^1$H NMR (CDCl₃): δ=0.82-1.82 (m, 11H, 1'-H, 3-,2'-,4'-,5'-,6'-H₂), 0.89/0.91 (2s, 6H, 3'-Me₂), 1.10/1.11 (2s, 3H, 2-Me), 1.20/1.23 (2d, J=6.0 Hz, 3H, 5-Me), 1.93-2.09 (m, 2H, 4-H₂), 3.94-4.09 (m, 1H, 5-H).-$^{13}$C NMR (CDCl₃): δ=21.2/21.3/21.9/22.4/23.3/24.2/24.4/24.7 (q, 2-,5-Me, 3'-Me axial), 22.5/22.6 (2t, C-5'), 27.6/27.7/27.8/ 27.8 (4t, C-3), 30.7/30.8 (2s, C-3'), 33.7/33.8 (2q, 3'-Me equat.), 33.7/34.0/34.5/35.2/35.6/36.1 (6t, C-4, -6'), 39.4/ 40.8/41.0/41.2 (4t, C-2', -4'), 43.2/43.4/43.5/43.6 (4d, C-1'), 73.4/73.5/75.0/75.1 (4d, C-5), 85.0/85.1 (2s, C-2).-MS (EI): m/e (%)=43 (38) [$C_3H_7^+$], 55 (9) [$C_4H_7^+$], 69 (6) [$C_5H_9^+$], 81 (3) [$M^+$-$C_8H_{15}$—H₂O], 99 (100) [$M^+$-$C_8H_{15}$], 111 (3) [$C_8H_{15}^+$], 138 (1) [$C_{10}H_{18}^+$], 177 (1) [$M^+$-$CH_3$—H₂O], 195 (2) [$M^+$-$CH_3$].

Odor description: Sweet, floral-fruity, with green and blackcurrant-like facets.

EXAMPLE 11

Fruity-Floral Accord for Female Perfumes

| | Ingredient | Parts per weight |
|---|---|---|
| 1. | Benzyl acetate | 40 |
| 2. | 2-Cyclohexyl-2-phenylacetonitrile | 80 |
| 3. | Damascenone at 1% in dipropylene glycol | 30 |
| 4. | γ-Decalactone | 4 |
| 5. | 3,7-Dimethyloct-6-en-1-ol | 10 |
| 6. | 1,1-Dimethyl-2-phenylethyl acetate | 20 |
| 7. | 1,1-Dimethyl-2-phenylethyl butanoate | 20 |
| 8. | Ethyl butanoate | 10 |
| 9. | Ethyl maltol at 10% in dipropylene glycol | 4 |
| 10. | Ethyl 2-methylbutanoate | 2 |
| 11. | Geraniol | 240 |
| 12. | 1a,3,3,4,6,6-Hexamethyl-1a,2,3,4,5,6,7,7a-octahydronaphtho[2,3-b]oxirene at 50% in triethyl citrate | 50 |
| 13. | (3Z)-Hex-3-en-1-ol | 4 |
| 14. | (3Z)-Hex-3-en-1-yl acetate | 4 |
| 15. | 2-Hexylcyclopent-2-en-1-one at 10% in DPG | 12 |
| 16. | 2-Hexyl-3-phenylprop-2-enal | 80 |
| 17. | 3-(4-Isobutylphenyl)-2-methylpropanal | 200 |
| 18. | Methyl dihydrojasmonate | 80 |
| 19. | 8-Methyl-α-ionone | 60 |

| Ingredient | Parts per weight |
|---|---|
| 20. γ-Undecalactone | 10 |
| 21. 2-tert-Butyl-5-methyl-2-propyltetrahydrofuran | 40 |
| | 1000 |

2-tert-Butyl-5-methyl-2-propyltetrahydrofuran adds to this floral-fruity raspberry accord a sophisticated blackcurrant note, which conveys diffusivity, freshness and naturalness. Moreover, this compound rounds the composition off and increases the volume, without incorporating unpleasant sulphury connotation as is usually the case when employing blackcurrant odorants. Thereby, it turns this otherwise plain fruity accord into a solid foundation for a multifacet female fragrance.

EXAMPLE 12

Fruity-Green Fantasy Fragrance for Use in Cosmetics

| Ingredient | Parts per weight |
|---|---|
| 1. 1,3-Benzodioxole-5-carboxaldehyde | 16 |
| 2. 2-tert-Butylcyclohexyl acetate | 80 |
| 3. Coumarin | 24 |
| 4. Dihydromyrcenol | 80 |
| 5. Ethyl acetoacetate | 32 |
| 6. Ethyl 1,3-dioxolan-2-yl-2-methylacetate | 16 |
| 7. Ethyl 3-methyl-3-phenylglycidate | 4 |
| 8. Ethyl oxyhydrate | 4 |
| 9. (3Z)-Hex-3-en-1-yl acetate at 10% in DPG | 8 |
| 10. Hexyl acetate | 16 |
| 11. 4-(4-Hydroxyphenyl)-2-butanone (N112) at 10% in DPG | 8 |
| 12. α-Ionone | 16 |
| 13. Iso-E-Super | 32 |
| 14. Linalool | 160 |
| 15. Linalyl acetate | 130 |
| 16. Nonyl acetate | 50 |
| 17. 3-Phenylprop-2-enal | 4 |
| 18. 4-Methoxybenzaldehyde | 80 |
| 19. 8-Methyl-α-ionone | 160 |
| 20. 5-Methyl-3-heptanone oxime | 16 |
| 21. 1,7,7-Trimethyl-2'-(isopropyl)spiro-(bicyclo[2.2.1]heptane-2,4'-[1,3]dioxane) at 50% in isopropyl myristate | 32 |
| 22. γ-Undecalactone | 32 |
| 23. 2-(3',3'-Dimethylcyclohexyl)-2,5-dimethyl-2,5-dihydrofuran | 10 |
| | 1010 |

Though 2-(3',3'-dimethylcyclohexyl)-2,5-dimethyl-2,5-dihydrofuran is used in 1% only, it harmonizes the composition with a sophisticated, sparkling touch of blackcurrant. It brings naturalness to the composition and rounds off the fruity aspects of this fantasy fragrance for use in cosmetics.

EXAMPLE 13

Red Berries Fragrance for Use in Shampoo

| Ingredient | Parts per weight |
|---|---|
| 1. Allyl hexanoate | 0.40 |
| 2. Allyl pentyloxyacetate | 0.50 |
| 3. Benzaldehyde | 2.00 |
| 4. 1,3-Benzodioxole-5-carboxaldehyde | 6.00 |
| 5. 2-tert-Butylcyclohexyl acetate | 70.00 |
| 6. 4-tert-Butylcyclohexyl acetate | 1.00 |
| 7. 2-Cyclohexyl-2-phenylacetonitrile | 5.00 |
| 8. α-Damascone | 1.00 |
| 9. Decanal | 0.60 |
| 10. Dihydromyrcenol | 15.00 |
| 11. Dihydro-5-pentyl-2(3H)-furanone | 10.00 |
| 12. 2,4-Dimethylcyclohex-3-enecarboxaldehyde | 4.00 |
| 13. 3,7-Dimethylnona-2,6-dienenitrile | 0.20 |
| 14. 3,7-Dimethylnona-1,6-dien-3-ol | 60.00 |
| 15. 1,1-Dimethyl-2-phenylethyl butanoate | 3.00 |
| 16. Dipropylene glycol (DPG) | 57.91 |
| 17. Dodecahydro-3a,6,6,9a-tetramethyl-naphto-(2,1b)-furan | 0.10 |
| 18. Ethyl acetate | 1.00 |
| 19. Ethyl acetoacetate | 1.00 |
| 20. Ethyl butanoate | 0.20 |
| 21. Ethyl 2-ethyl-6,6-dimethylcyclohex-2-enecarboxylate | 5.00 |
| 22. Ethyl heptanoate | 1.00 |
| 23. Ethyl maltol | 0.10 |
| 24. Ethyl 2-methylbutanoate | 2.00 |
| 25. 6-Ethyl-3-methyloct-6-en-1-ol | 5.00 |
| 26. Ethyl 3-methyl-3-phenylglycidate | 7.00 |
| 27. trans-8-Ethyl-1-oxaspiro[4.5]decan-2-one at 1% in triethyl citrate | 2.00 |
| 28. Ethyl vanillin | 0.05 |
| 29. 4,6,6,7,8,8-Hexamethyl-1,3,4,6,7,8-hexahydrocyclopenta[g]benzopyran at 75% in diethyl phthalate | 400.00 |
| 30. Hexyl salicylate | 140.00 |

| Ingredient | Parts per weight |
|---|---|
| 31. 1-(4-Hydroxyphenyl)butan-3-one | 70.00 |
| 32. β-Ionone | 28.00 |
| 33. Isoamyl acetate | 5.00 |
| 34. Iso-E-Super | 50.00 |
| 35. (−)-p-Menthan-3-ol | 0.50 |
| 36. 4,7-Methano-1H-3a,4,5,6,7,7a-hexahydro-inden-6-yl acetate | 5.00 |
| 37. 4-Methoxybenzaldehyde | 0.50 |
| 38. Methoxyphenylbutanone | 2.00 |
| 39. Methyl anthranilate | 0.20 |
| 40. 4-Methyldec-3-en-5-ol | 0.20 |
| 41. Methyl dihydrojasmonate | 40.00 |
| 42. 2-Methyl-3-(4-isopropylphenyl)propanal | 1.30 |
| 43. (E)-Methyl octa-4,7-dienoate | 0.30 |
| 44. (10Z)-13-Methyloxacyclopentadec-10-en-2-one | 5.00 |
| 45. cis-2-Methyl-4-propyl-1,3-oxathiane at 50% in triethyl citrate | 0.09 |
| 46. Phenoxyethyl isobutanoate | 243.00 |
| 47. 2-Phenylethanol | 30.00 |
| 48. 1-Phenylethyl acetate | 2.00 |
| 49. Prenyl acetate | 0.30 |
| 50. 2,4,4,7-Tetramethylnona-6,8-dien-3-one oxime at 1% in benzyl laurate | 0.50 |
| 51. 1-(2,6,6-Trimethyl-2-cyclohexen-1-yl)hepta-1,6-dien-3-one | 0.05 |
| 52. γ-Undecalactone | 5.00 |
| 53. 2-(3',3'-Dimethylcyclohexyl)-2,5-dimethyl-2,5-dihydrofuran | 10.00 |
| | 1300 |

In a dosage of less than 1%, 2-(3',3'-dimethylcyclohexyl)-2,5-dimethyl-2,5-dihydrofuran adds to the composition a fruity, juicy aspect that imparts a sweet, sugary yet natural tonality. The dihydrofuran blends very well with the other compounds of this fruity fragrance, makes it rounder and more complex. Its blackcurrant note harmonizes very well with the musk and the floral ionone accord, without dominating the fragrance.

The invention claimed is:

1. A compound of formula (I)

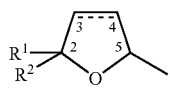

wherein $R^1$ is methyl, ethyl, propyl or iso-propyl;

$R^2$ is a branched $C_4$-$C_7$ alkyl, with the proviso that the $C_5$ alkyl is neo-pentyl, $C_5$-$C_8$ cycloalkyl, or monomethyl dimethyl-substituted $C_5$ or $C_6$ cycloalklyl; and the bond between C-3 and C-4 is a single bond, or the dotted line together with the bond between C-3 and C-4 represents a double bond.

2. A compound according to claim 1 selected from the group consisting of 2-tert-butyl-5-methyl-2-propyl-2,5-dihydrofuran, 2-tert-butyl-5-methyl-2-propyltetrahydrofuran, 2-tert-butyl-2-isopropyl-5-methyl-2,5-dihydrofuran, 2-tert-butyl-2-isopropyl-5-methyltetrahydrofuran, 2-tert-butyl-2-ethyl-5-methyl-2,5-dihydrofuran, 2-tert-butyl-2-ethyl-5-methyltetrahydrofuran, 2-tert-butyl-2,5-dimethyl-2,5-dihydrofuran, 2-tert-butyl-2,5-dimethyltetrahydrofuran, 2-(3',3'-dimethylcyclohexyl)-2,5-dimethyl-2,5-dihydrofuran, and 2-(3',3'-dimethylcyclohexyl)-2,5-dimethyltetrahydrofuran.

3. A method for using a compound as an odorant, the method comprising/mixing a compound of formula (I) or a composition comprising a compound of formula (I) in a fragrance application/wherein the compound of formula (I) comprises the odorant described by the chemical structure:

wherein $R^1$ is methyl, ethyl, propyl or iso-propyl, $R^2$ is a branched $C_4$-$C_7$ alkyl, $C_5$-$C_8$ cycloalkyl, or monomethyl or dimethyl-substituted $C_5$ or $C_6$ cycloalkyl; and the bond between C-3 and C-4 is a single bond, or the dotted line together with the bond between C-3 and C-4 represents a double bond.

4. The method of claim 3 wherein the compound of formula (I) is selected from the group consisting of 2-tert-butyl-5-methyl-2-propyl-2,5-dihydrofuran, 2-tert-butyl-5-methyl-2-propyltetrahydrofuran, 2-tert-butyl-2-isopropyl-5-methyl-2,5-dihydrofuran, 2-tert-butyl-2-isopropyl-5-methyltetrahydrofuran, 2-tert-butyl-2-ethyl-5-methyl-2,5-dihydrofuran, 2-tert-butyl-2-ethyl-5-methyltetrahydrofuran, 2-tert-butyl-2,5-dimethyl-2,5-dihydrofuran, 2-tert-butyl-2,5-dimethyltetrahydrofuran, 2-(3',3'-dimethylcyclohexyl)-2,5-dimethyl-2,5-dihydrofuran, and 2-(3',3'-dimethylcyclohexyl)-2,5-dimethyltetrahydrofuran.

5. A flavour or fragrance composition comprising a compound of formula (I) wherein the compound of formula (I) is described by the chemical structure:

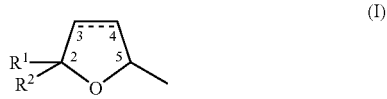

wherein $R^1$ is methyl, ethyl, propyl or iso-propyl:

$R^2$ is a branched $C_4$-$C_7$ alkyl, $C_1$-$C_8$ cycloalkyl, or monomethyl or dimethyl-substituted $C_5$ or $C_6$ cycloalkyl; and the bond between C-3 and C-4 is a single bond, or the dotted line together with the bond between C-3 and C-4 represents a double bond.

6. The composition of claim 5 wherein the compound of formula (I) is selected from the group consisting of 2-tert-butyl-5-methyl-2-propyl-2,5-dihydrofuran, 2-tert-butyl-5-methyl-2-propyltetrahydrofuran, 2-tert-butyl-2-isopropyl-5-methyl-2,5-dihydrofuran, 2-tert-butyl-2-isopropyl-5-methyltetrahydrofuran, 2-tert-butyl-2-ethyl-5-methyl-2,5-dihydrofuran, 2-tert-butyl-2-ethyl-5-methyltetrahydrofuran, 2-tert-butyl-2,5-dimethyl-2,5-dihydrofuran, 2-tert-butyl-2,5-dimethyltetrahydrofuran, 2-(3',3'-dimethylcyclohexyl)-2,5-dimethyl-2,5-dihydrofuran, and 2-(3',3'-dimethylcyclohexyl)-2,5-dimethyltetrahydrofuran.

7. A method of manufacturing a flavour or fragrance composition, the method comprising: incorporating a compound of formula (I) into a base material, wherein the compound of formula (I) is described by the chemical structure:

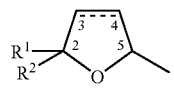

(I)

wherein $R^1$ is methyl ethyl, propyl or iso-propyl;

$R^2$ is a branched $C_4$-$C_7$ alkyl $C_5$-$C_8$ cycloalkyl, or monomethyl or dimethyl-substituted $C_5$ or $C_6$ cycloalkyl; and the bond between C-3 and C-4 is a single bond, or the dotted line together with the bond between C-3 and C-4 represents a double bond.

8. The method of claim 7 wherein the compound of formula (I) is selected from the group consisting of 2-tert-butyl-5-methyl-2-propyl-2,5-dihydrofuran, 2-tert-butyl-5-methyl-2-propyltetrahydrofuran, 2-tert-butyl-2-isopropyl-5-methyl-2,5-dihydrofuran, 2-tert-butyl-2-isopropyl-5-methyltetrahydrofuran, 2-tert-butyl-2-ethyl-5-methyl-2,5-dihydrofuran, 2-tert-butyl-2-ethyl-5-methyltetrahydrofuran, 2-tert-butyl-2,5-dimethyl-2,5-dihydrofuran, 2-tert-butyl-2,5-dimethyltetrahydrofuran, 2-(3',3'-dimethylcyclohexyl)-2,5-dimethyl-2,5-dihydrofuran, and 2-(3',3'-dimethylcyclohexyl)-2,5-dimethyltetrahydrofuran.

9. A method of manufacturing a fragrance application, comprising the incorporation of a compound of formula (I) into a base material, wherein the compound of formula (I) is described by the chemical structure:

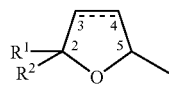

(I)

wherein $R^1$ is methyl, ethyl, propyl or iso-propyl;

$R^2$ is a branched $C_4$-$C_7$ alkyl, $C_5$-$C_8$ cycloalkyl, or monomethy or dimethyl-substituted $C_5$ or $C_6$ cycloalkyl; and the bond between C-3 and C-4 is a single bond, or the dotted line together with the bond between C-3 and C-4 represents a double bond.

10. The method according to claim 9 wherein the fragrance application is selected from the group consisting of perfumes, household products, laundry products, body care products and cosmetics.

11. The method of claim 9 wherein the compound of formula (I) is selected from the group consisting of 2-tert-butyl-5-methyl-2-propyl-2,5-dihydrofuran, 2-tert-butyl-5-methyl-2-propyltetrahydrofuran 2-tert-butyl-2-isopropyl-5-methyl-2,5-dihydrofuran, 2-tert-butyl-2-isopropyl-5-methyltetrahydrofuran, 2-tert-butyl-2-ethyl-5-methyl-2,5-dihydro furan, 2-tert-butyl-2-ethyl-5-methyltetrahydrofuran, 2-tert-butyl-2,5-dimethyl-2,5-dihydrofuran, 2-tert-butyl-2,5-dimethyltetrahydrofuran, 2-(3',3'-dimethylcyclohexyl)-2,5-dimethyl-2,5-dihydrofuran, and 2-(3',3'-dimethylcyclohexyl)-2,5-dimethyltetrahydrofuran.

12. The method of claim 9 wherein the proportion of the compound of formula (I) is from 0.001 to 5 weight percent of the fragrance application.

13. The method of claim 9, wherein the incorporation of the compound of formula (I) is by directly admixing the compound of formula (I) to the fragrance application.

14. The method of claim 9, wherein the incorporation of the compound of formula (I) is by admixing a fragrance composition comprising a compound of formula (I) and mixing the fragrance composition with the fragrance application.

15. The method of claim 9, including entrapping the compound of formula (I) with an entrapment material, and then mixing with the fragrance application.

* * * * *

UNITED STATES PATENT AND TRADEMARK OFFICE
CERTIFICATE OF CORRECTION

PATENT NO.       : 7,632,790 B2  
APPLICATION NO.  : 10/589654  
DATED            : December 15, 2009  
INVENTOR(S)      : Philip Kraft Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 292 days.

Signed and Sealed this

Second Day of November, 2010

David J. Kappos  
*Director of the United States Patent and Trademark Office*